United States Patent
Weyl et al.

[11] Patent Number: 6,150,607
[45] Date of Patent: Nov. 21, 2000

[54] CABLE BUSHING FOR CONNECTING AT LEAST ONE CABLE OF A GAS SENSOR

[75] Inventors: Helmut Weyl, Schwieberdingen; Hans-Martin Wiedenmann, Stuttgart, both of Germany

[73] Assignee: Robert Bosch GmbH, Stuttgart, Germany

[21] Appl. No.: 09/109,436

[22] Filed: Jul. 2, 1998

[30] Foreign Application Priority Data

Jul. 3, 1997 [DE] Germany ................ 197 28 370

[51] Int. Cl.$^7$ .................................................. H02G 3/18
[52] U.S. Cl. ............... 174/65 G; 174/135; 174/153 G; 248/56; 16/2.1; 439/604
[58] Field of Search .................. 174/65 G, 65 SS, 174/135, 151, 152 G, 153 G; 16/2.1, 2.2; 248/56; 439/604, 274

[56] References Cited

U.S. PATENT DOCUMENTS

| | | | |
|---|---|---|---|
| 4,832,615 | 5/1989 | Thakrar et al. | 439/272 |
| 4,912,287 | 3/1990 | Ono et al. | 174/153 G |
| 5,189,779 | 3/1993 | Fishel et al. | 29/453 |
| 5,567,916 | 10/1996 | Napiorkowski et al. | 174/153 G |
| 5,959,250 | 9/1999 | Daoud | 174/65 R |

FOREIGN PATENT DOCUMENTS 195 40 022  4/1997  Germany .

*Primary Examiner*—Kristine Kincaid
*Assistant Examiner*—Dhiru R Patel
*Attorney, Agent, or Firm*—Kenyon & Kenyon

[57] ABSTRACT

An arrangement for sealing a cable bushing for at least one connecting cable, and in particular for a connecting cable of a sensor element of a gas sensor. On the terminal side, the sensor element is arranged in a metallic housing which has a tubular opening, in which a sealing arrangement is disposed, through which the connecting cable is conducted. The sealing arrangement is fixedly surrounded by the housing and has an elastically deformable sealing element and a spring element acting in the direction of the leading-through of the connecting cable, the sealing element being elastically deformed by the spring energy of the spring element.

7 Claims, 1 Drawing Sheet

CABLE BUSHING FOR CONNECTING AT LEAST ONE CABLE OF A GAS SENSOR

FIELD OF THE INVENTION

The present invention relates to an arrangement for sealing a cable bushing for at least one connecting cable, and in particular for a connecting cable of a sensor element of a gas sensor.

BACKGROUND INFORMATION

A sealing arrangement of cable bushings is described, for example, in German Patent Application No. 195 40 022, in which connecting cables are passed through lengthwise-running bore holes of a sealing device made of plastic such as PTFE (polytetrafluor ethylene), and the sealing device is fixedly surrounded by a housing part, with the assistance of a crimped connection. The cable bushing is subject to high temperature stress, particularly in the case of gas sensors in exhaust systems of internal combustion engines. Because of the variable thermal expansion behaviors of the different materials of the sealing device made of PTFE, and of the housing part made of steel, a gap appears between the sealing device and the housing part as a result of the temperature stress and the temperature fluctuations. Thus, between the sealing device and the housing part, it is necessary to insert an additional sealing ring, e.g. a Viton O-ring, which, because of its elasticity, permanently seals off the gap. A gap can likewise develop at the boundary position between the PTFE sealing device and the cable insulation. To permanently close this gap, the cable insulation is fused to the material of the PTFE sealing device. However, this procedure requires an additional manufacturing step. In addition, the two materials must be matched with one another.

SUMMARY OF THE INVENTION

In contrast, the arrangement according to the present invention is advantageous in that it permits a temperature-resistant sealing of the cable bushing. The spring element acting in the axial direction provides for the necessary contact pressure of the high-temperature-resistant sealing element, both on the cable insulation and on the housing part, and thus forms a reliable seal between the connecting cables and the sealing element, as well as between the housing part and the sealing element. The sealing arrangement of the present invention exhibits a perceptibly higher temperature resistance, since a flow of the PTFE material which is utilized, for example, is compensated to the greatest extent possible by the axially-acting spring element. It is preferable that the spring energy act in the axial direction, i.e. in the direction of the leading-through of the cable connections.

It is also advantageous to insert the sealing element and the spring element between two structural members that are axially fixed in position in the opening of the housing part, the one structural member forming a supporting structure for the spring element, and the other structural member forming a counterpart for the sealing element. The sealing element is elastically deformed between the two structural members by the force of the spring element. The crimped connection tamped to the connecting cables, in cooperation with the one axially fixed structural member, form a strain relief for the connecting cables.

DETAILED DESCRIPTION

Figure 1:
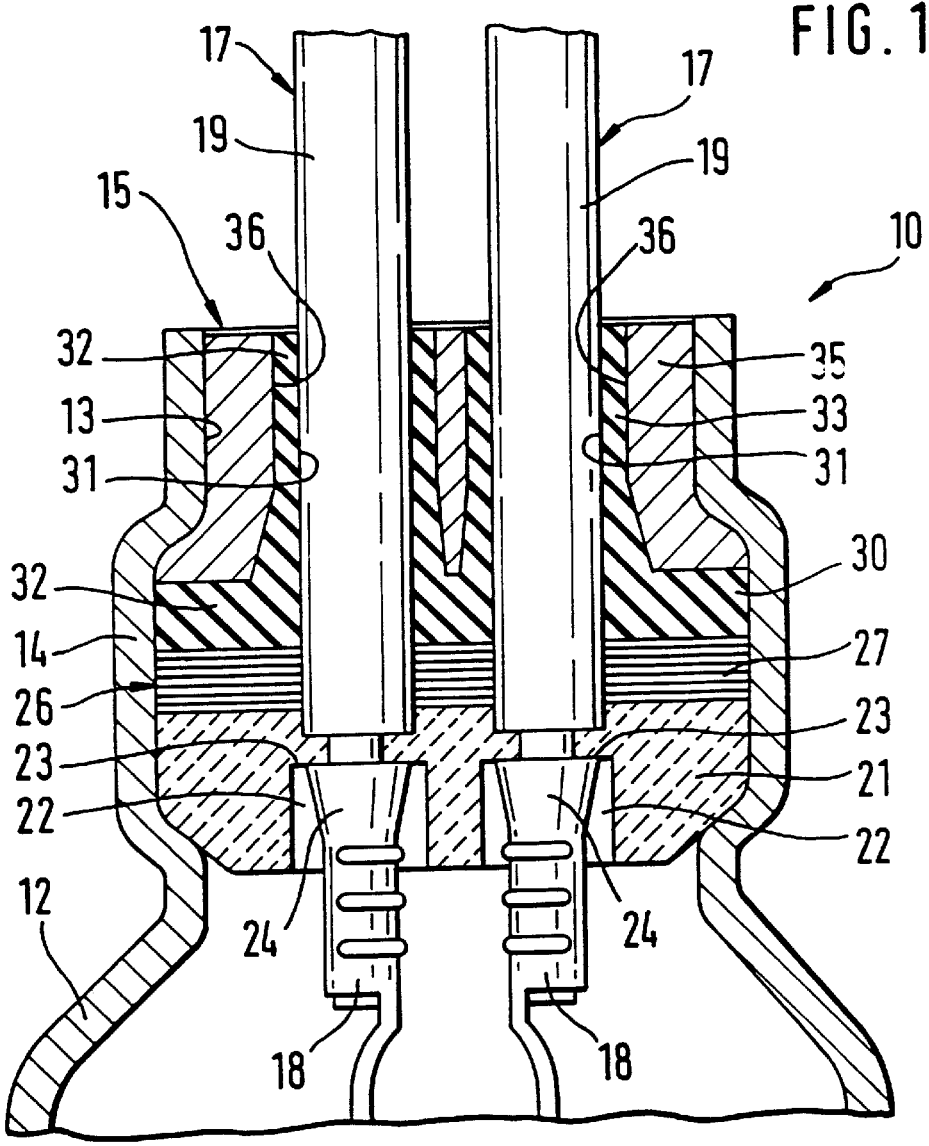
FIG. 1 shows a sectional view of a cable bushing of a gas sensor according to a first embodiment of the present invention.

FIG. 1 shows an intersection through a cable bushing 10 in the installed state in a gas sensor such as a lambda probe. Cable bushing 10 includes a housing part 12 made, for example, of steel, and shown only in-the cut-away portion. At the end section, housing part 12 has a tubular opening 13, in which is located a sealing arrangement 15. For example, two connecting cables 17, each having a cable insulation 19, penetrate sealing arrangement 15 and are each provided with a crimped connection 18 at their probe-inner end. Sealing arrangement 15 is tamped in housing part 12, which is why housing part 12 has a toroidally-shaped bulge 14 in the area of tubular opening 13.

Sealing arrangement 15 has a supporting structure 21 fixed in position in opening 13, a spring element 26 acting in the axial direction, a one-piece, elastically deformable sealing element 30, as well as a counterpart 35 likewise fixed in position in opening 13.

Because of the contact with crimp connections 18, supporting structure 21 is constructed from an electrically insulating material, for example as a ceramic machined part having lengthwise-running, first lead-throughs 22 for connecting cables 17, lead-throughs 22 each having a graded offset 23 pointing inwardly. Crimp connections 18, tamped to connecting cables 17, have a widening section 24 which abuts against graded offset 23, so that a strain relief is formed for connecting cables 17.

Figure 2:
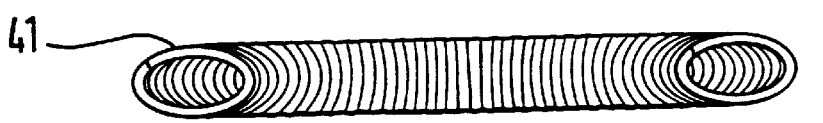
FIG. 2 shows a sectional view of the axially acting spring element according to a second embodiment of the present invention.
Figure 3:
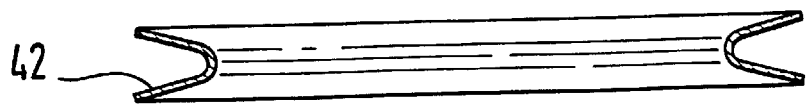
FIG. 3 shows a sectional view of the axially acting spring element according to a third embodiment of the present invention.
Figure 4:
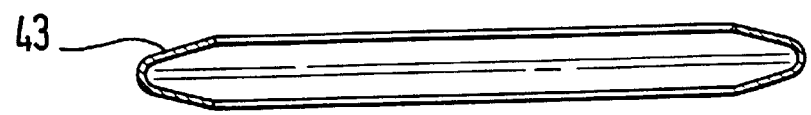
FIG. 4 shows a sectional view of the axially acting spring element according to a fourth embodiment of the present invention.

Mounted on supporting structure 21 is spring element 26 acting in the axial direction. According to a first embodiment shown in FIG. 1, spring element 26 is made up of superimposed mica washers 27. Alternatively, axially acting spring element 26 can be made from an elastic graphite foil, a pre-sintered, steatite, machined part, a pre-pressed (e.g., rough-pressed) ceramic-fiber material, a coated, metallic-screen disk made of stainless steel, corrugated, thin, metal foils made of stainless spring steel, a cup spring, or from a combination of the constructions indicated. Further embodiments according to the present invention are shown in FIGS. 2, 3 and 4.

Resting on spring element 26 is elastically deformable sealing element 30 made, for example, of an elastomer. For example, a parafluorelastomer (PFKM) can be used as elastomer. Sealing element 30 has the form of a disk-shaped base plate 32, on which tubular sleeve members 33 are premolded corresponding to the number of connecting cables 17. Base plate 32 fills up the cross-section of opening 13. As in the case of ceramic machined part 21 (i.e., supporting structure), two lead-throughs 31 for connecting cables 17 are introduced in sealing element 30, the connecting cables in each case being surrounded by tubular sleeve members 33. Tubular sleeve members 33 extend in the longitudinal direction of the bushing of the connecting cables, for example, over the remaining length of sealing arrangement 15.

Moreover, counterpart 35 is arranged over elastic sealing element 30. Provided in counterpart 35 are three lead-throughs 36 in which sleeve bodies 33 of sealing element 30 are inserted. Counterpart 35 grips bulge 14 from behind, so that counterpart 35 is axially fixed in position in the direction of the axial force emanating from spring element 26.

The sealing action of sealing arrangement 15 is attained, in that the force emanating from spring element 26 and acting in the axial direction, affects sealing element 30 which is pressed against counterpart 35. On the reverse side, spring element 26 is braced against ceramic machined part 21 fixed in position in opening 13. In this context, sealing element 30 becomes elastically deformed and positions itself both against the wall of opening 13, and, with sleeve members 33, against cable insulations 19 of connecting cables 17. The third lead-throughs 36 form an outer support for sleeve members 33, so that sleeve bodies (members) 33 press to the greatest extent possible over the entire length against cable insulation 19. The prestress acting through spring element 26 on sealing element 30 compensates for the varying thermal expansion behaviors of the different materials of housing part 12 and sealing element 30.

Further embodiments for spring element 26, acting in the axial direction, are shown in FIGS. 2, 3 and 4. FIG. 2 illustrates a flattened volute spring washer 41, for instance, which is inserted in place of mica washers 27 between ceramic machined part 21 and sealing element 30. To improve the distribution of the compressive forces, it is preferable to provide a metal disk between volute spring washer 41 and sealing element 30. FIG. 3 shows a cross-section through an annular spring element 42 having a V-shaped cross-section, the V-shape pointing inwardly. FIG. 4 shows a likewise annular spring element 43 having a V-shaped cross-section, where the V-shape points outwardly. It is preferable in the case of annular spring elements 42,43 as well, to place a metal disk underneath toward sealing element 30.

The use of the sealing arrangement of the present invention is not limited to the lambda probes described. Further application cases are conceivable, in which connecting cables must be brought out of a housing via a cable bushing, and the cable bushing must form a hermetic seal in the housing.

What is claimed is:

1. An arrangement for sealing a cable bushing for at least one connecting cable, the at least one connecting cable including a first end extending though an opening in a housing, the arrangement comprising:

a sealing arrangement situated in the opening in the housing, the sealing arrangement including:

an elastically deformable sealing element, and a spring element, a spring force of the spring element acting in an axial direction with respect to the first end of the at least one connecting cable, wherein the sealing element is elastically deformed by the spring force of the spring element.

2. The arrangement according to claim 1, further comprising:

two members situated in the opening in the housing and being at least axially maintained in a predetermined position, one of the two members positioned behind another one of the two members in the direction of the first end of the at least one connecting cable, wherein the sealing element and the spring element are positioned between the two members.

3. The arrangement according to claim 2, wherein one of the two members is a supporting structure for the spring element, and another one of the two members is a counterpart element for the sealing element, and wherein the sealing element is elastically deformed when the sealing element is pressed against the counterpart element by the force of the spring element.

4. The arrangement according to claim 3, wherein the supporting structure includes a ceramic machined part having at least one graduated lead-through portion receiving the at least one connecting cable, and wherein the at least one connecting cable is coupled to a crimp connection, the crimp connection including a widening portion which widens toward the at least one connecting cable, the widening portion gripping the at least one graduated lead-through portion from a rear end of the at least one connecting cable.

5. The arrangement according to claim 1, wherein the sealing element includes a disk-shaped member having a first lead-through portion, the first lead-through portion receiving the at least one connecting cable, the disk-shaped member substantially filling a cross-section of the opening in the housing, and wherein the sealing arrangement further includes a sleeve member premolded on the disk-shaped member at the first lead-through portion, the sleeve member surrounding the at least one connecting cable at the first lead-through portion.

6. The arrangement according to claim 5, further comprising:

a counterpart including second lead-through portions, wherein the sleeve member is inserted through the second lead-through portions.

7. The arrangement according to claim 1, wherein the at least one connecting cable is a cable of a sensor element of a gas sensor.

* * * * *